US007258676B2

(12) United States Patent
Calderon et al.

(10) Patent No.: US 7,258,676 B2
(45) Date of Patent: Aug. 21, 2007

(54) DEVICE AND METHOD FOR LOW PRESSURE COMPRESSION AND VALVE FOR USE IN THE SYSTEM

(75) Inventors: Noam A. Calderon, Haifa (IL); Amit Ben Dror, Tzurit (IL)

(73) Assignee: C-Boot Ltd, Kibbutz Yiron (IL)

( * ) Notice: Subject to any disclaimer, the term of this patent is extended or adjusted under 35 U.S.C. 154(b) by 0 days.

(21) Appl. No.: 10/865,447

(22) Filed: Jun. 10, 2004

(65) Prior Publication Data

US 2005/0027221 A1 Feb. 3, 2005

Related U.S. Application Data

(63) Continuation-in-part of application No. 09/602,224, filed on Jun. 23, 2000, now Pat. No. 6,589,194.

(60) Provisional application No. 60/477,656, filed on Jun. 11, 2003.

(51) Int. Cl.
*A61F 5/00* (2006.01)

(52) U.S. Cl. ........................... 602/13; 602/20; 602/23; 602/75

(58) Field of Classification Search .................. 602/13, 602/20, 23, 75; 128/869, 876, 877, 878, 128/882, 868
See application file for complete search history.

(56) References Cited

U.S. PATENT DOCUMENTS 1,608,239 A 11/1926 Rosett
3,774,611 A * 11/1973 Tussey ....................... 417/274
4,029,087 A 6/1977 Dye et al. ................. 128/24 R
4,372,297 A * 2/1983 Perlin .......................... 128/64
4,467,426 A * 8/1984 Hida et al. .................. 364/424
4,677,767 A 7/1987 Darby ......................... 36/102
4,841,956 A * 6/1989 Gardner et al. ............... 128/64
5,117,812 A 6/1992 McWhorter ............... 128/24 R
5,120,300 A 6/1992 Shaw .......................... 602/61

(Continued)

FOREIGN PATENT DOCUMENTS

EP 0168 085 1/1986

(Continued)

*Primary Examiner*—Henry Bennett
*Assistant Examiner*—Dinnatia Doster-Greene
(74) *Attorney, Agent, or Firm*—Rashida A. Karmali

(57) ABSTRACT

The present invention relates generally to compression devices and, more particularly to a method using air flow to close the exhaust valve in each sleeve, allows air to fill the sleeve to a pretuned pressure, and finally deflating the sleeve by letting the air flow through the outlet valve. This creates a pressure gradient and a pneumatic cycle means that facilitates the massaging movement on the limb towards direction of the heart. The magnetic force in valves is uniquely adapted for controlling low-pressure compression. A magnetically adjustable valve is adapted for use in a compression device to control and regulate low to very low pressures and comprising of a movable magnetic part and a metal part, defining an air gap there between. A self-powered device causes the magnetic part and the metal part to move away from each other and control the air access and pressure in the valve body, while creating a gradient of decreasing pressure, the highest pressure being in the first air chamber to the lowest pressure in the last air chamber.

17 Claims, 3 Drawing Sheets

U.S. PATENT DOCUMENTS

| | | | | | |
|---|---|---|---|---|---|
| 5,179,941 | A | * | 1/1993 | Siemssen et al. | 128/40 |
| 5,254,122 | A | | 10/1993 | Shaw | 606/201 |
| 5,259,415 | A | * | 11/1993 | Hess et al. | 137/625.65 |
| 5,263,473 | A | | 11/1993 | McWhorter | 128/25 R |
| 5,569,297 | A | | 10/1996 | Makower et al. | 606/201 |
| 5,632,298 | A | * | 5/1997 | Artinian | 137/102 |
| 5,634,889 | A | * | 6/1997 | Gardner et al. | 601/151 |
| 5,711,760 | A | | 1/1998 | Ibrahim et al. | 601/149 |
| 5,897,518 | A | | 4/1999 | Shaw | 602/65 |
| 5,913,902 | A | | 6/1999 | Geible | 623/55 |
| 5,989,204 | A | | 11/1999 | Lina | 601/152 |
| 6,007,559 | A | * | 12/1999 | Arkans | 606/201 |
| 6,290,662 | B1 | | 9/2001 | Morris et al. | 601/149 |
| 6,319,215 | B1 | | 11/2001 | Manor et al. | 601/152 |
| 6,355,008 | B1 | | 3/2002 | Nakao | 601/150 |
| 6,361,512 | B1 | | 3/2002 | Mackay et al. | 601/150 |
| 6,447,467 | B1 | | 9/2002 | Barak | 601/149 |
| 6,558,338 | B1 | * | 5/2003 | Wasserman | 601/52 |
| 6,585,669 | B2 | | 7/2003 | Manor et al. | 601/152 |
| 6,685,661 | B2 | | 2/2004 | Peled | 601/149 |

FOREIGN PATENT DOCUMENTS

| | | |
|---|---|---|
| GB | 2 263 405 | 7/1993 |

* cited by examiner

DEVICE AND METHOD FOR LOW PRESSURE COMPRESSION AND VALVE FOR USE IN THE SYSTEM

CROSS-REFERENCE TO OTHER APPLICATION

This application is a Continuation-in-part of Provisional application Ser. No. 60/477,656, filed on Jun. 11, 2003, which in turn is a Continuation-in-Part of application Ser. No. 09/602,224, filed Jun. 23, 2000, and issued as U.S. Pat. No. 6,589,194 on Jul. 8, 2003, which references are all incorporated herein in its entirety.

FIELD OF THE INVENTION

The present invention relates to self-powered compression devices and methods for promoting circulation by applying low pressure compression. It is a self-powered system driven by atmospheric air drawn into the system at every step. More particularly, the invention is in the class of medical devices, comprising an inlay legging, a plurality of sleeves or balloons, which utilize sequential, cyclical pressure to aid circulation in a body part such as the limb of a mammal. The present invention relates generally to compression devices and, more particularly, to a method and device for low pressure compression using a ladder like support structure for the plurality of sleeves or balloons positioned and tuned such that the first sleeve has the highest pressure and each one above it has a lower pressure than the one below, by adjusting the magnetic field of control valves adapted for controlling low-pressure compression. The sleeves may be placed in any order along the limb so long as a) the pressure is maintained the highest in the first sleeve, b) the pressure in the second sleeve is equal to or lower than the pressure in the first sleeve, and c) the pressure in the third sleeve is equal to or lower than the pressure in the second sleeve, and so on. The unique feature of the decreasing pressure means lies in the sequence in which the sleeves are connected (first sleeve having the highest pressure and the last sleeve having the lowest pressure) and not in the placement of the sleeve.

BACKGROUND TO THE INVENTION

There are many patented devices that apply cyclic pressure to a mammal's limb, arm or foot. In conventional compression devices, the pulsating pads or plunges for improving circulation may be mechanically, hydraulically, or electrically actuated. Elastic and non-elastic stockings, hydraulic and pneumatic bladders or inflatable sleeves may be used to apply controlled levels of compression to an animal's limbs or other body parts. Most suffer varying degrees of shortcomings, including ineffectiveness, difficulties in application and removal, lack of controlled adjustability, loss of compression, excessive sweating, foul odor and discomfort.

These earlier contributions in the art are described in U.S. Pat. No. 5,117,812 to McWhorter; U.S. Pat. No. 5,254,122 to Shaw; U.S. Pat. No. 5,263,473 to McWhorter; U.S. Pat. No. 5,897,518 to Shaw; U.S. Pat. No. 5,989,204 to Lina; U.S. Pat. No. 6,355,008 to Nakao; and U.S. Pat. No. 6,447,467 to Barak. U.S. Pat. No. 5,120,300 and U.S. Pat. No. 5,254,122 relate to therapeutic devices capable of applying therapeutic compression to the body, particularly the limbs, arms and/or feet, in which the user applies non-elastic therapeutic compression band by band, and the user can tighten the compression bands to control the non-elastic pressure. The cyclical and sequential compression of limbs improves blood fluid returns for reducing edema and improving healing.

U.S. Pat. No. 5,897,518 describes a foot and ankle therapeutic compression device in which a pair of foot and ankle compression bands are tightened and anchored in tightened condition by Velcro hook and loop surfaces.

U.S. Pat. No. 5,375,430 describes a gravity powered shoe air conditioner including a compression-expander type cooling or heating system incorporated into a heel of the shoe, and is powered by reciprocal gravity pressure upon the shoe which occurs naturally during walking.

U.S. Pat. No. 5,711,760 describes a self-inflating venous boot comprising a first air chamber having a flexible wall portion adapted to be situated adjacent to the outer surface of the leg, a second air chamber underneath the person's heel, this second chamber forces air out of it when the person's heel bears downward, a conduit means for permitting air flow between the first and second air chambers, whereby air flows between the first and second air chambers. Air flows from the second chamber into the first chamber and pressure cyclically increases in the first chamber urging the wall portion against the leg when the person's heel presses downward on the second chamber. Similarly, air flows from the first to second chamber and pressure on the leg is reduced when the person's heel stops pressing on the second chamber. Some of the disadvantage of this system are: 1) it is not adapted to regulate low-pressure changes 2) it is not automatic 3) it is not tunable and 4) it is not sequential.

In a co-pending U.S. application Ser. No. 09/602,224, now issued as U.S. Pat. No. 6,589,194, is described a self-powered compression device that permits a wearer of a plurality of inflatable sleeves around the limb to apply a controlled level of circular compression to the limb. The self-powered compression device improves the circulation and healing in a variety of vascular circulation problems. However, the device described in the above patent is not adapted to control and regulate low-pressure changes, and therefore optimal performance is not achieved.

The present invention is directed at overcoming one or more of the problems described above.

SUMMARY OF THE INVENTION

The self-powered compression device of the invention comprises a plurality of inflatable sleeves, a foot pump and a device for distributing compressed air from a compressed air source to the plurality of sleeves that use the compressed air. The device further includes a ladder-like support structure having a plurality of valve bodies, a plurality of inlet valves for connecting the valve bodies to the compressed air source, a plurality of outlet valves, each adapted to communicate with at least one sleeve that uses compressed air, and a plurality of exhaust valves outside the device. The ladder-like support structure referred herein as a "descending pressure ladder", comprises a means for providing decreasing pressure in each of the inter-connected sleeves, positioned above the sleeve near the foot, such that the highest pressure is in the first sleeve and the lowest pressure is in the last sleeve.

The pneumatic control system of the invention creates a cycle of air flow by closing the exhaust valve in each sleeve, allows air to fill the sleeve through the inlet valve to a pretuned pressure, and finally deflates the sleeve by letting the air flow through the outlet valve. This creates a pressure gradient that facilitates the massaging movement on the limb towards direction of the heart.

The unique aspect of the present invention is to set a defined pressure in the sleeves, and to provide a means of accumulating atmospheric air into the sleeves, transmitting the air from sleeve to sleeve, and allowing the air to deflate at the end of each cycle. This creates a pneumatic pressure control system that operates in sequential pressure cycles. For example, each cycle starts when the wearer takes a step, the pressure increases, this seals the exhaust valves and allows the first sleeve to fill up through a tunable inlet valve. Then the second sleeve starts to fill to a tunable pressure, and so on until the pressure reaches a preset level in each sleeve. This is then followed by activating the relief valve and opening the exhaust valves to allow deflation of air from the sleeves.

The present invention also provides a plurality of magnetically adjustable valves movably provided in each valve body, adapted for generating low pressure that can be used to create a comfortable massaging action without the disadvantage of causing extreme constriction of the swollen body part. In one aspect of the present invention a magnetically adjustable valve adapted for use in a compression device for generating low pressure is disclosed. The magnetically adjustable valve comprises a valve body, a valve orifice, a plastic tube placed inside the valve body, a magnetic ring element, said ring element being wrapped around a plastic tube, a metallic ball and a metallic cylinder wrapped around the plastic tube. The plastic tube uses is threaded at one end, wherein the magnetic ring is screwed in place. At the second end of the plastic tube is placed the metal ball, said metal ball having a diameter larger than the diameter of the plastic tube. Thus, the metal ball covers the opening or orifice of the plastic tube, thereby closing the plastic tube and trapping the air inside the plastic tube. The distance between the magnetic ring element at one end of the tube and the metal ball located at the second end of the tube determines and controls the pressure level in the plastic tube and the access of air in the tube.

The magnetic valves come in different shapes and operate on the principle of differential pressure between the high power required to break the metallic part from the magnet and the low power needed to bring back the metal ball towards the magnet by using the magnetic force attraction. The pressure level is adjusted by adjusting the distance between the metal ball and the magnet. No electrical current is required to create the electromagnetic circuit in the present invention.

In an alternate embodiment of the magnetic valve means, a metallic cylinder is used in combination with a magnetic part to control the air flow into each sleeve or between sleeves. The shape of the two elements generating the magnetic force and differential power may be flat, and be suitable for use as a vascular valve in blood vessels, or in weather forecast equipment.

In another embodiment of the present invention, the magnetic valve provides an accurate control of the air pressure by detecting very low pressure changes in the range of about 15 mmHg, for example, in compression devices using low pressures such as in vascular pumps, pneumatic walking devices, weather forecast equipment or vacuum-based equipment, all at an affordable cost.

In a preferred embodiment of the present invention the magnetic power of the magnetic ring is sufficiently strong so that when the magnetic ring is separated from the metal ball, the magnetic attraction between the magnetic ring and the metal ball reduces by a factor of square ($X^2$) in relation to the distance between the magnetic ring and the metal ball.

BRIEF DESCRIPTION OF THE FIGURES

For a better understanding of the present invention, reference may be made to the accompanying drawings in which.

DETAILED DESCRIPTION OF THE PREFERRED EMBODIMENTS

The present invention provides a pneumatic pressure control system that operates in sequential pressure cycles. For example, each cycle starts when the wearer takes a step, atmospheric air enters the system, pressure increases, this seals the exhaust valves and allows the first sleeve to fill up through a tunable inlet valve. Then the second sleeve starts to fill to a tunable pressure, and so on until the pressure reaches a preset level in each sleeve. This is then followed by activating the relief valve and opening the exhaust valves to allow deflation of air from the sleeves.

Figure 1:
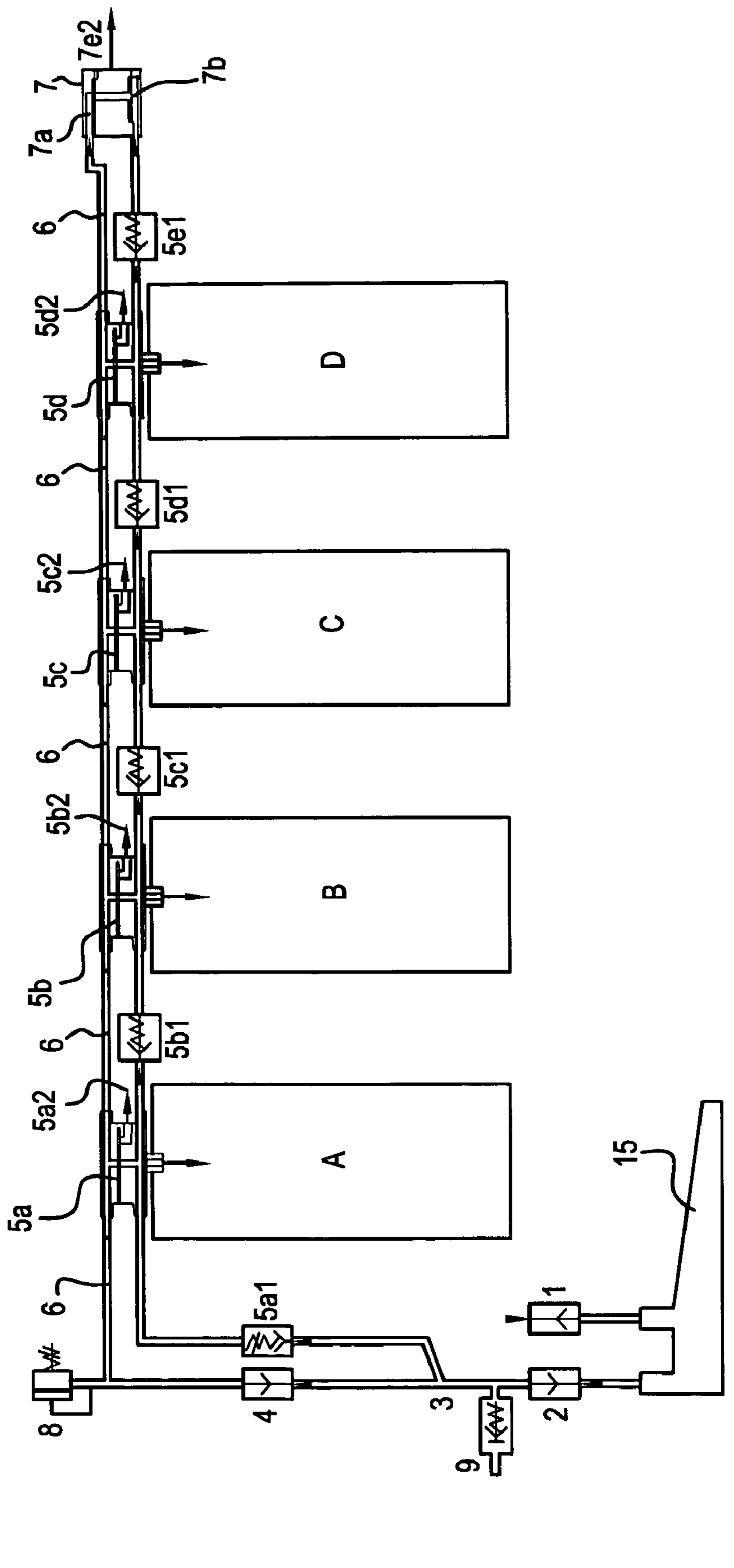
FIG. 1 is a schematic diagram of compression device represented in a ladder-like support structure.

FIG. 1 describes a system, wherein the pressure of each individual inter-connected chamber is higher than the pressure in the chamber immediately above, or superior to, and less than the pressure in the chamber immediately below, or inferior to, said individual chamber.

In FIG. 1, the atmospheric air is pumped into the foot pump through the inlet valve 1. The foot pump 15 compresses the air into the control system through inlet check valve 2. The compressed atmospheric air is then split through a Y connector 3, after which it reaches a check valve 4 and a controllable magnetically operated check valve **5*a*1. Passage through the controllable magnetically operated check valve 5*a*1 is harder than passage through check valve 4, therefore the air passing through check valve 4, interrupts the air flow in tube 6. This creates pressure on inlet valves 5*a*, 5*b*, 5*c*, and 5*d*. In addition, the entrance of air through 7*a*, creates pressure on an unloading relief valve 7. This prevents the air from exhausting toward the atmosphere through holes 5*a*2, 5*b*2, 5*c*2, 5*d*2, and 7*e*2. After preventing the atmospheric air from leaving the device, continuous pulsating airflows arrive from the foot pump. Once said air flows build up a sufficient amount of pressure, said pressure breaks through the controllable magnetically operated check valve 5*a*1, and said air flow starts to inflate sleeve A and reach the controllable magnetically operated check valve 5*b*1**.

Atmospheric air then accumulates in sleeve A, until it reaches a preset pressure threshold specific to sleeve A. Once said preset pressure threshold is reached said atmospheric air breaks through the controllable magnetically operated check valve **5*b*1, and starts to inflate sleeve B and reach the controllable magnetically operated check valve 5*c*1**.

The atmospheric air then accumulates in sleeve B, increasing the pressure inside it until it reaches the preset pressure threshold specific to sleeve B. Once said preset pressure threshold is reached in sleeve B, the pressure breaks through the controllable magnetically operated check valve **5*c*1, starts to inflate sleeve C and allows atmospheric air to reach the controllable magnetically operated check valve 5*d*1**.

The atmospheric air then accumulates in sleeve C, increasing the pressure inside until it reaches the preset pressure threshold specific to sleeve C. Once said preset pressure threshold is reached in sleeve C, the pressure breaks through the controllable magnetically operated check valve **5*d*1, starts to inflate sleeve D and allows atmospheric air to reach the controllable magnetically operated check valve 5*e*1**.

The atmospheric air then accumulates in sleeve D, increasing until it reaches the preset pressure threshold specific to sleeve D. Once said preset threshold is reached in sleeve D, the pressure breaks through the controllable magnetically operated check valve **5*e*1, into entrance 7*b*, opens up unloading relief valve 7, exhausts the interrupted air out of blocking tube 6 through hole 7*e*2 to the atmosphere, and by this action opens up outlet valves 5*a*, 5*b*, 5*c*, and 5*d*, to allow the inflated sleeves A, B, C, and D to deflate the air to the atmosphere through holes 5*a*2, 5*b*2, 5*c*2, 5*d*2**.

The pressure on those sleeves decreases until it reaches its preset constant pressure, thus completing the cycle. The cycle creates intermittent sequential graduated pressure on the limb and stimulating blood flow. The cycle repeats continually until the patient stops the walking, at which time pressure remains constant according to the preset constant pressure.

This is the principle of the decreasing or descending pressures in the sleeves of air chambers supported by 6the ladder-like support structure system, wherein pressure in the blocking tube 6, will always be higher then the pressure in sleeve A, the pressure in sleeve A will always be higher then the pressure in sleeve B, and so on until the relief valve 7.

The number of sleeves is not limited and the system might contain different number of sleeves. The self-powered pressure device may comprise a bandage which can be used to wrap around the sleeves.

The self-powered pressure device may also include a ventilating means between the leg and the inflatable sleeves. The ventilating means may include two perforated layers, said one layer being above said other layer and having a gap about 1 to 5 mm between them to allow air flow.

The self-powered pressure device may further comprise a second set of sleeves, said sleeves being placed between the first set of sleeves and the leg. The second set of sleeves may be inflated partially or fully.

Each of the controllable magnetically operated check valves, **5*a*1, 5*b*1, 5*c*1, 5*d*1, and 5*e*1 serves as safety system to sleeves A, B, C, and D, by enabling the passage of extra pressure from one sleeve to the following one, and so on, until extra pressure passing through the controllable magnetically operated check valve 5*e*1, activates the relief valve 7**, thereby causing deflation and relieving the pressure from the sleeves.

In order to increase safety, blocking tube 6, which has the highest pressure in the system during the inflation, contains an additional overload relief valve 8. This valve relieves the pressure from tube 6, and consequently from the sleeves, in the event that something has gone wrong and the system is experiencing higher pressure then should be present.

When uncoupled, the end is protected or blocked by check valve 9. However, it is possible to connect the system to an external power source, if the patient wishes to stop walking or taking steps so as to activate the intermittent system by external power source.

Figure 2:
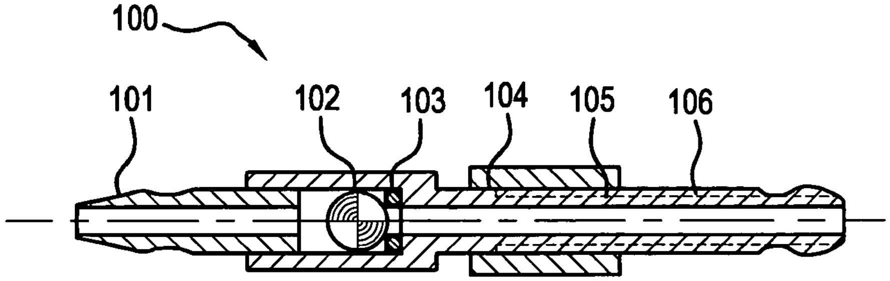
FIG. 2 is a cross sectional view of a first embodiment of a magnetic valve.

Controllable magnetically operated check valves **5*a*1, 5*b*1, 5*c*1, 5*d*1, and 5*e*1 operate on the principle of the magnet valves, as described in FIG. 2**, wherein each magnetic valve comprises a valve body having at one end an orifice and at a second end a magnetic cylinder, said magnetic cylinder being affixed to the valve body by a screw member, said screw member being positioned adjacent to a magnetic ring, a metallic ball having a diameter greater than the diameter of the valve body is positioned between said orifice and said magnetic ring, and a magnetic circuit is controlled by adjusting the distance between said magnetic ring and a magnetic ball.

Referring now to the drawings, wherein the magnetic valve used in the first embodiment of the present invention is shown, FIG. 2 illustrates a magnetic valve 100. The valve 100 includes a valve body 106 that houses a magnetic cylinder 104 at one end by means of a nut mechanism 105, and has an orifice 101 at the second end. A metallic ball 102 having a diameter greater than the diameter of the valve body 106, is positioned adjacent a rubber gasket ring 103. The magnetic cylinder 104 is screwed to the valve body 106 by a threading means, or by any other means, such that the forces that attach the metal ball 102 towards the rubber gasket ring 103 will be altered by the magnetic forces acting between the magnetic cylinder 104 and the metal ball 102.

In one aspect of the present invention, the magnetically adjustable valve 100 comprises a magnetic cylinder element 104, said cylinder element 104 being wrapped around a valve body 106, which may be optionally made of a plastic tubular material. The valve body 106 has at one end a threaded portion for screwing in place the magnetic cylinder 104. The valve body 106 comprises a second end wherein is positioned a metal ball 102; said metal ball having a diameter that is larger than the diameter of the valve body 106. The metal ball 102 covers the orifice of the rubber gasket ring 103 thereby closing the air access out of the valve body 106. The distance between the magnetic cylinder 104 and the metal ball 102 controls the pressure in the valve body 106 and provides a means for controlling low to very low air pressures.

The magnetic valve 100 may be used in different shapes (e.g., magnetic gasket) and may not be limited to the cylinder 104 or the metal ball 102. The magnetic valve 100 of the present invention may be used in a variety of compression devices, self powered pumps or systems tapping air or energy generated during walking or any such movement by an animal. The pressure control may be through airflow, gas or fluid flow. For example, the magnetic valve 100 of the present invention may be adapted for use as a vascular valve inside a vein or an artery, or in weather forecasting equipment, or even a pressure-unloading valve in a pneumatic or hydraulic system.

Thus, while the present invention has been particularly shown and described with reference to the preferred embodiment above, it will be understood by those skilled in the art that various additional embodiments may be contemplated without departing from the spirit and scope of the present invention.

The operation of the present invention is now described with reference to FIG. 3 and FIG. 4 to illustrate the features and advantages associated with the present invention.

Figure 3:
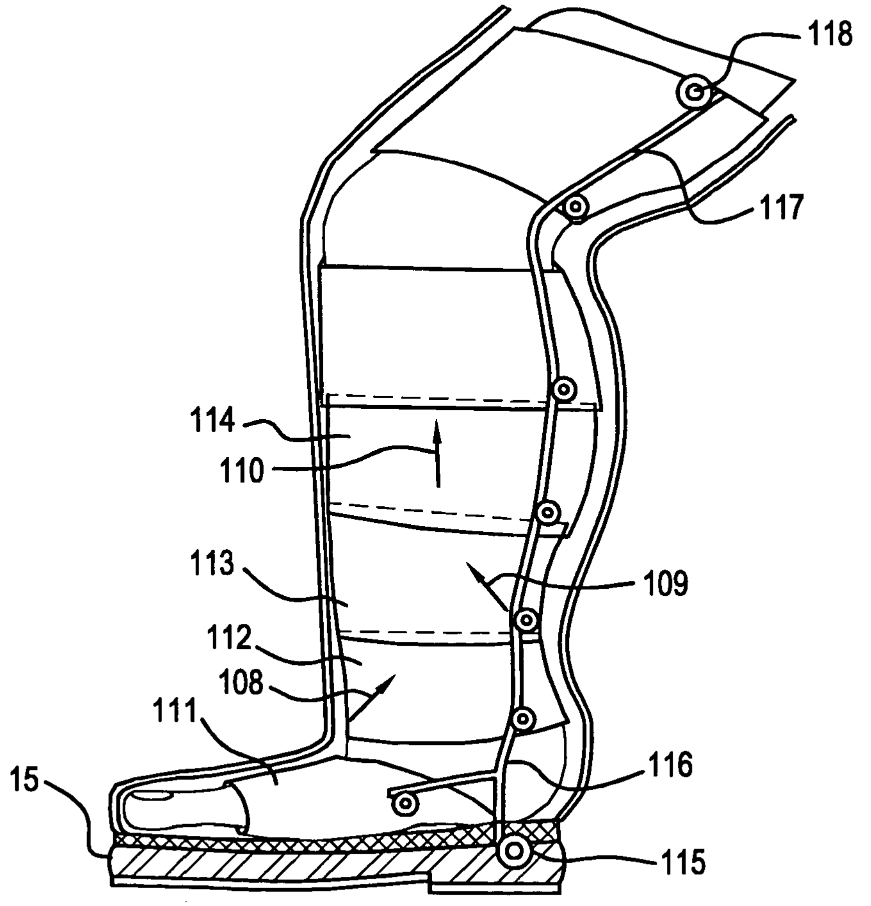
FIG. 3 is a schematic diagram illustrating a magnetically controlled valve used in combination with a self-powered compression device (see FIG. 1) described in the co-pending U.S. application Ser. No. 09,602,224, issued as U.S. Pat. No. 6,589,194. It is a lateral view of an embodiment comprising of a pump, bandage, inflatable pressure sleeves, pneumatic pipe system, an outlet valve, an inlet valve, an exhaust valve and a magnetic valve.
Figure 4:
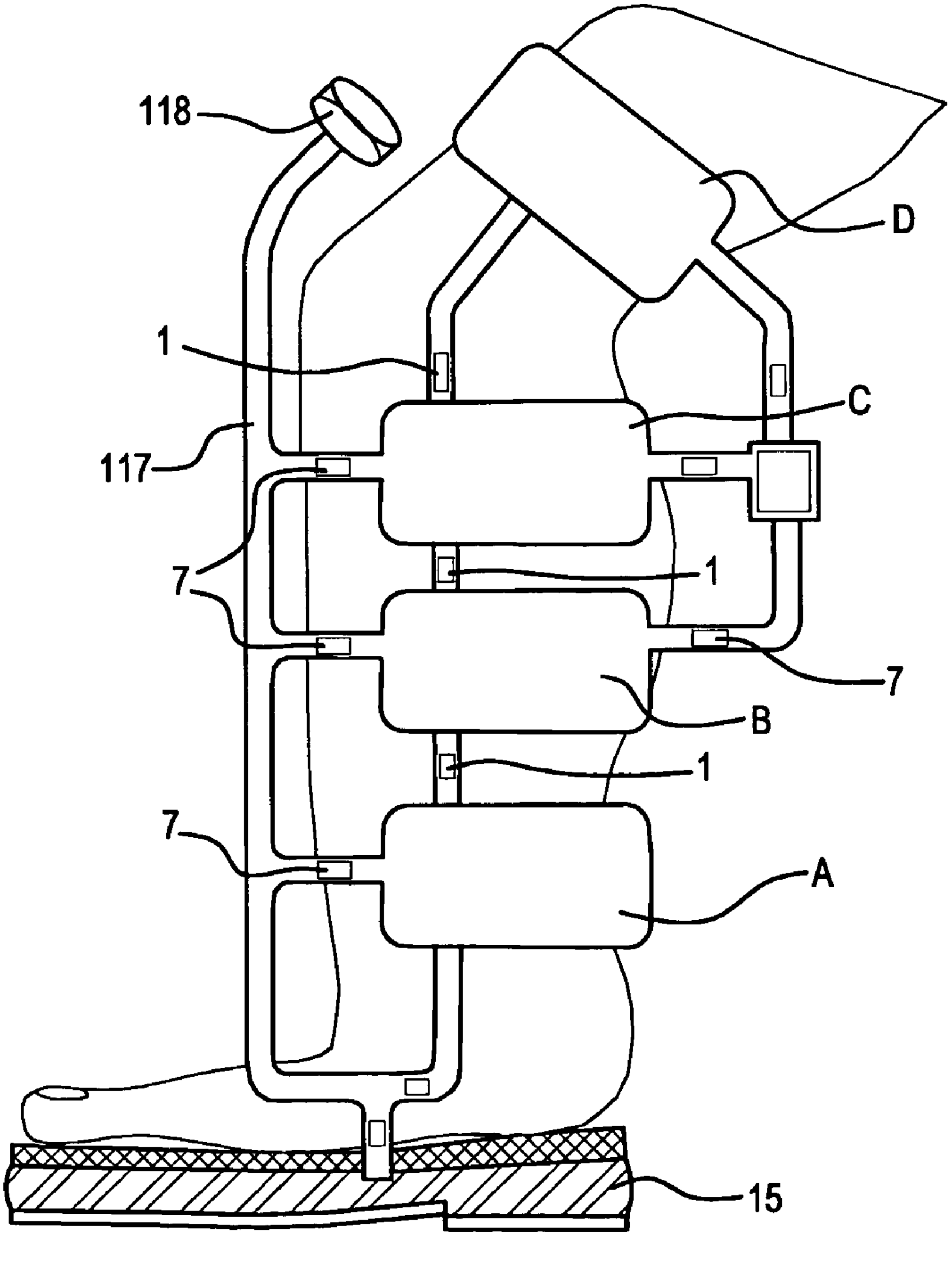
FIG. 4 is a schematic diagram illustration, a lateral view of a second embodiment of the compression device showing the structure of the pipe system for the device.

In the various embodiments of the compression device described in FIG. 3, FIG. 4, and FIG. 1, the intended application of the magnetic valve is its use in controlling low to very low pressures.

Each pressure sleeve has an inlet valve 1 which is used to inflate the sleeve with air or liquid, and an outlet valve 7 which allows the air or liquid to flow out in a sequential and cyclical pumping action. When the wearer flexes the muscles, as in walking or shift in weight, the resulting vector forces 108 and 109, create a compression and massaging effect in the direction 110, flowing from the distal sleeve 111 to the proximal sleeve, which is closest to the heart.

In FIG. 3, at one end of the pump 15 including a power supply is affixed the portal 115, which is also located at one end of the piping system 116. This continues longitudinally as a piping system along the back side of the limb and is connected in sequence to each of the sleeves through an inlet valve and an exit valve 7. At the other end, the piping system 117 ends into an exhaust valve 118.

In FIG. 4, the pump 15 including a power supply is placed on the underside of the heel of the foot. The pneumatic piping system 117 extends from the pump along the limb and ends into the exhaust valve 118. Extending from the piping system 117 are a series of outlet valves 7 each of which connects to a sleeve A, B, C or D.

FIG. 4 exemplifies another application of the pneumatic system, wherein sleeve D functions as a pressure check to blood in the venous system. For example, when all sleeves reach the pre-tuned pressure, this leads to deflation of air from sleeves A, B and C through relief valve 118. However, the pressure in sleeve D is held constant, and this prevents the venous blood from flowing towards the foot in between pneumatic cycles. Furthermore, when the next cycle starts leading to inflation of sleeves A and B, this causes sleeve D to deflate and the pressure is transmitted to sleeve C. Once sleeve C reaches its pre-tuned pressure, this leads sleeve D to inflate to its pre-tuned pressure. This in turn leads to deflation of sleeves A, B and C through valve 118, while the pressure in sleeve D is held constant, and the cycle repeats.

The self-powered pressure device of the invention further comprises ventilated stratum between the leg and the inflatable sleeves. The stratum includes two perforated layers, said one layer being above said other layer and having a gap about 1 to 5 mm between them to allow air flow between the two perforated layers. The ventilated stratum therefore allows the exhausting air to reach and ventilate the human limb.

The self-powered pressure device according to the invention, also has an embodiment wherein the relief valve uses the same principle of differential pressure as in the exhaust valves of the sleeves, and further includes a means for creating deformation (in the form of a pin or an equivalent structure that can deform the membrane-not shown herein) to cause release of pressure and air trapped in the sleeves without needing electricity. Other aspects, objects and advantages of the present invention can be obtained from a study of the drawings, the disclosure and the appended claims. The present invention is not to be limited in scope by the embodiment disclosed in the example which is intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Those skilled in the art will recognize, or be able to ascertain using no more than routine experimentation, any equivalents to the specific embodiments of the invention described herein. Such equivalents are intended to be encompassed by the claims.

What is claimed is:

1. A self-powered compression device comprising:

a foot pump, said pump connected to a pneumatic pressure control system, wherein atmospheric air is drawn into said system at each step, the pneumatic pressure control system comprising a plurality of inflatable sleeves, each of said sleeves connected to valve bodies, each of said valve bodies having a set of inlet magnetic check valves and outlet exhaust valves for connecting to the compressed air source and supplying compressed air to the inflatable sleeves, wherein the pressure in said inflatable sleeves is controlled by a magnetically operated check valve to provide suitable pressures for massaging and promoting health, the self-powered pressure device further comprising an inlet valve, wherein each step brings new atmospheric air into the device, inflating and deflating the sleeves in continuous cycles according to pre-tuned pressure in each of the sleeves and wherein the magnetically operated check valve includes:

a valve body having an orifice at one end and a magnetic cylinder at the other end, wherein the magnetic cylinder is attached to the valve body by a screw member, the screw member is positioned adjacent to a magnetic ring, and a metallic ball having a diameter greater than the diameter of the valve body is placed between the orifice and the magnetic ring.

2. The self-powered pressure device according to claim 1, wherein the magnetic force between the magnetic ring and the metallic ball is controlled by the distance between them, said magnetic force controlling the pressure in the sleeve attached to the magnetically operated valve.

3. The self-powered pressure device according to claim 2, wherein the magnetically operated valve is selected from a group consisting of different shapes, different sizes and different structures having varying magnetic forces between the magnetic part and the metallic part.

4. The self-powered pressure device according to claim 2 further comprising a bandage wrapped around the sleeves.

5. The self-powered pressure device according to claim 3 wherein the bandage is made from material including elastic material or non-elastic material.

6. The self-powered pressure device according to claim 3 wherein the bandage is part of the outer surface of the sleeves.

7. The self-powered pressure device according to claim 3 wherein the bandage is separate from the sleeves.

8. The self-powered pressure device according to claim 3 further comprising a ventilating means between the leg and the inflatable sleeves.

9. The self-powered pressure device according to claim 7 wherein the ventilating means includes two perforated layers, said one layer being above said other layer and having a gap about 1 to 5 mm between them to allow air flow.

10. The self-powered pressure device according to claim 1, further comprising a second set of sleeves, said sleeves being placed between the first set of sleeves and the leg.

11. The self-powered device according to claim 9, further comprising means for connecting to an external pressure source.

12. The self-powered device according to claim 1, further comprising means to reuse the released air into the system.

13. The self-powered pressure devise according to claim 1, wherein the pneumatic control system that builds up the sequential intermittent pressure cycle as well as control and distribute the pressure to the sleeves, works independently with any other pressure source.

14. A self-powered compression device comprising:

a foot pump, a pneumatic pressure control system comprising pressure relief valve and exhaust valves, wherein the opening of said system to exhaust the air and the closing of the system to trap the air in the sleeves, is execute automatically using only the air flow and does not depend on an electrical signal, the pneumatic system further comprising a plurality of inflatable sleeves, each of said sleeves connected to valve bodies, each of said valve bodies having a set of inlet and outlet valves for connecting to a compressed air source and supplying air to the inflatable sleeves, wherein the pressure in said inflatable sleeves is controlled by a magnetically operated metering check valve to provide suitable pressures for massaging and promoting health wherein the exhaust valves in the pneumatic system include an elastic membrane having differential pressure on either side of the membrane, and said membrane faces on one side an exhaust orifice of the sleeve, thus enabling the sealing of the sleeve exhaust orifice even when the pressure is equal or lower than the pressure within the sleeves.

15. The self-powered pressure device according to claim 14, wherein the relief valve uses the same principle of differential pressure as in the exhaust valves of the sleeves, and further includes a means for creating deformation in the membrane to cause release of pressure and air trapped in the sleeves without needing electricity.

16. The self-powered pressure device according to claim 14, wherein the magnetically operated check valve operates by using the magnetic force between the magnetic part and a metallic part to control the pressure level and transmission in the system.

17. The self-powered pressure device according to claim 14, further comprising an inlet valve, wherein each step brings new atmospheric air into the device, and inflating and deflating the sleeves in continuous cycles according to the pretuned pressure in each sleeve.

* * * * *